(12) United States Patent
Hotta

(10) Patent No.: US 8,785,199 B2
(45) Date of Patent: Jul. 22, 2014

(54) CULTURE MEDIUM AND METHOD FOR INDUCING DIFFERENTIATION INTO ADIPOCYTES

(75) Inventor: Yoshiyuki Hotta, Tokyo (JP)

(73) Assignee: Fujirebio, Inc, Tokyo (JP)

( * ) Notice: Subject to any disclaimer, the term of this patent is extended or adjusted under 35 U.S.C. 154(b) by 252 days.

(21) Appl. No.: 13/202,720

(22) PCT Filed: Feb. 18, 2010

(86) PCT No.: PCT/JP2010/052454
§ 371 (c)(1),
(2), (4) Date: Aug. 22, 2011

(87) PCT Pub. No.: WO2010/095684
PCT Pub. Date: Aug. 26, 2010

(65) Prior Publication Data
US 2011/0306133 A1    Dec. 15, 2011

(30) Foreign Application Priority Data

Feb. 23, 2009   (JP) .................................. 2009-038977

(51) Int. Cl.
*C12N 5/00*   (2006.01)
*C12N 5/077*   (2010.01)

(52) U.S. Cl.
USPC ........................... 435/404; 435/325; 435/375

(58) Field of Classification Search
CPC .. C12N 5/0662; C12N 5/0692; C12N 5/0031; C12N 2500/38; C12N 2500/25; C12N 2500/36; C12N 2500/99; C12N 2506/00; C12N 5/0663
USPC ......................................... 435/325, 375, 404
See application file for complete search history.

(56) References Cited

U.S. PATENT DOCUMENTS

2004/0092011 A1* 5/2004 Wilkison et al. .............. 435/366
2006/0211606 A1   9/2006 Goldspink et al.

FOREIGN PATENT DOCUMENTS

EP    2 233 565 A1   9/2010

OTHER PUBLICATIONS

Lehrke et al. The Many Faces of PPARgamma. Cell 123, Dec. 16, 2005. p. 993-999.*
Rodriguez et al. Adipocyte differentiation of multipotent cells established from human adipose tissue. Biochemical and Biophysical Research Communications 315 (2004) 255-263.*
Sottile et al. Bone morphogenetic protein-2 stimulates adipogenic differentiation of mesenchymal precursor cells in synergy with BRL 49653 (rosiglitazone). FEBS Letters 475 (2000) 201-204.*
Bunnell et al. Adipose-derived stem cells: Isolation, expansion and differentiation. Methods 45 (2008) 115-120.*
Product Information on lysophosphatidic acid (LPA) from Sigma-Aldrich.com. p. 1-3 (1997).*
Extended European Search Report issued Dec. 14, 2012, in European Patent Application No. 10743810.3.
Pebay et al., "Essential Roles of Sphingosine-1-Phosphate and Platelet-Derived Growth Factor in the Maintenance of Human Embryonic Stems Cells," Stem Cells (2005), vol. 23, pp. 1541-1548.
Ryden et al., "Functional characterization of human mesenchymal stem cell-derived adipocytes," Biochemical and Biophysical Research Communications (2003), vol. 211, pp. 391-397.
Simon et al., "Lysophosphatidic Acid Inhibits Adipocyte Differentiation via Lysophosphatidic Acid 1 Receptor-dependent Down-regulation of Peroxisome Proliferator-activated Receptor γ 2," The Journal of Biological Chemistry (Apr. 15, 2005) vol. 280, No. 15, pp. 14656-14662.

* cited by examiner

*Primary Examiner* — Taeyoon Kim
(74) *Attorney, Agent, or Firm* — Birch, Stewart, Kolasch & Birch, LLP

(57) ABSTRACT

Disclosed are a culture medium, an additive, and a method for efficiently inducing the differentiation of mammalian somatic stem cells into cells having the characteristics of adipocytes under conditions of serum-free or low-serum culture medium. The culture medium for inducing the differentiation of mammalian somatic stem cells into adipocytes comprises a basal medium for culturing mammalian cells, an agent for inducing the differentiation of mammalian somatic stem cells into adipocytes, biotin, a ligand for endothelial cell differentiation gene (Edg) family receptors, vitamin C, and HEPES, which culture medium is serum-free or contains a low concentration of serum.

12 Claims, 3 Drawing Sheets

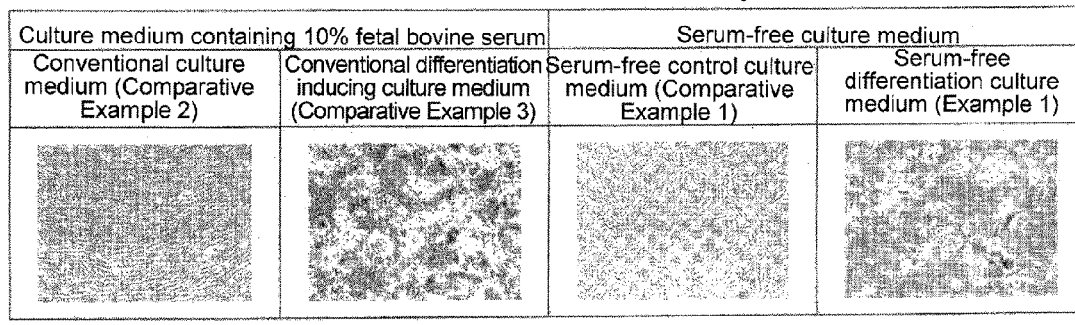

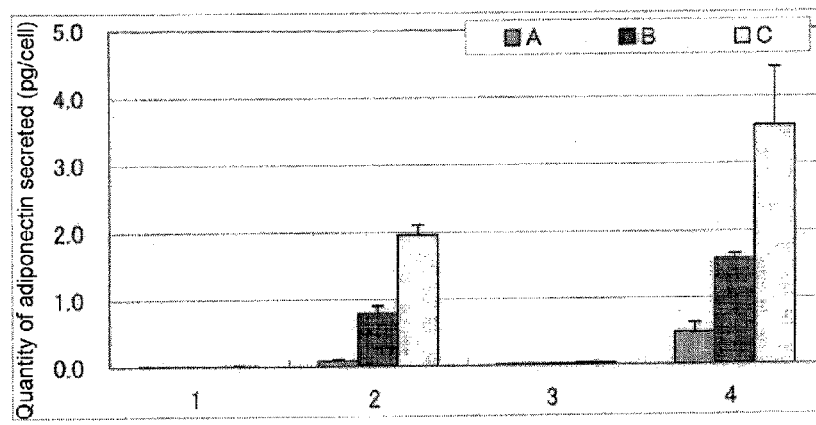

- A: Day 4 to Day 7 of differentiation induction
- B: Day 11 to Day 14 of differentiation induction
- C: Day 18 to Day 21 of differentiation induction
- 1: Conventional culture medium (Comparative Example 2)
- 2: Conventional differentiation culture medium (Comparative Example 3)
- 3: Serum-free control culture medium (Comparative Example 1)
- 4: Serum-free differentiation culture medium (Example 1)

(B)

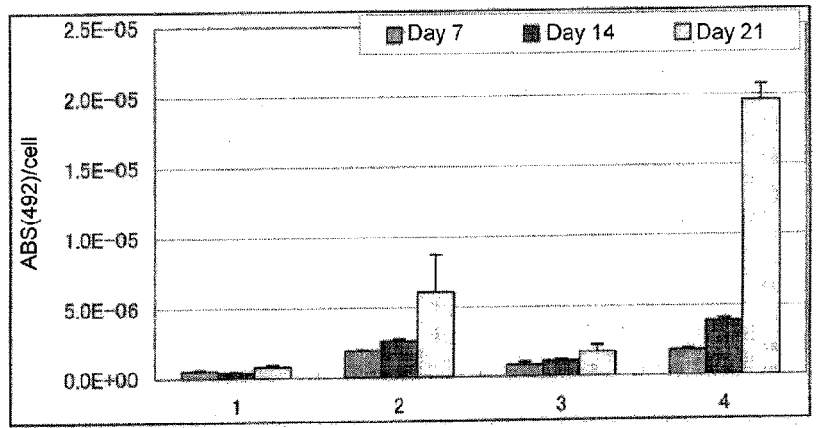

- 1: Conventional culture medium (Comparative Example 2)
- 2: Conventional differentiation culture medium (Comparative Example 3)
- 3: Serum-free control culture medium (Comparative Example 1)
- 4: Serum-free differentiation culture medium (Example 1)

Fig.2

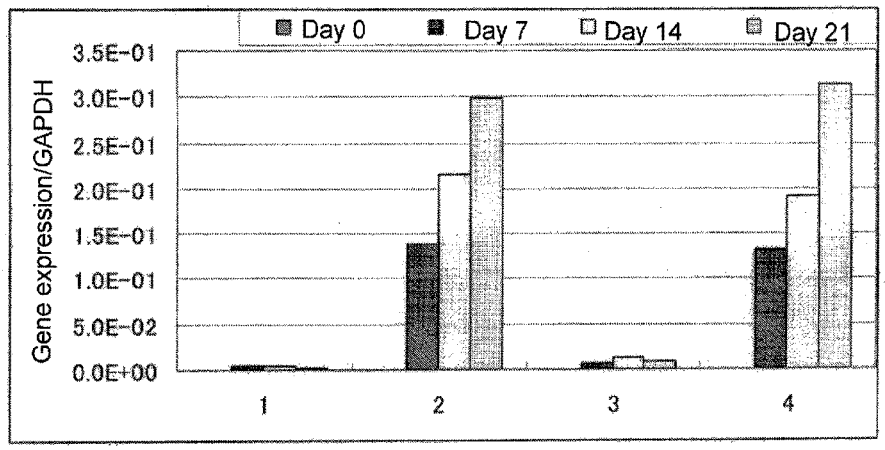
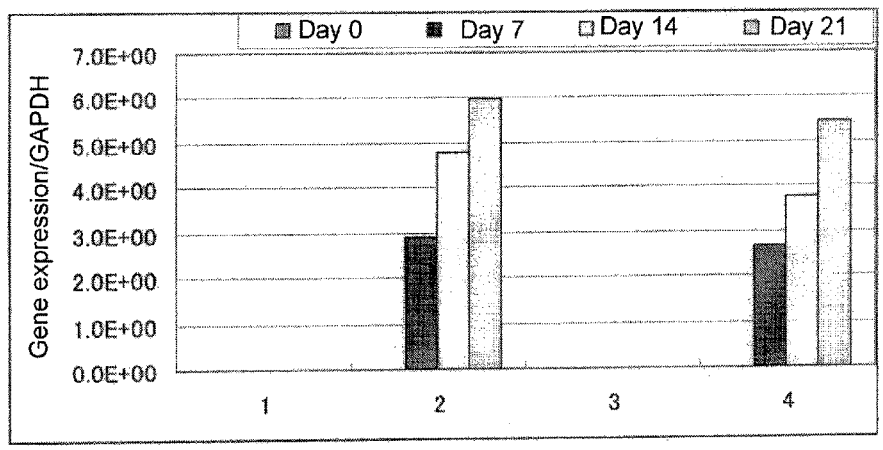
Fig.3

CULTURE MEDIUM AND METHOD FOR INDUCING DIFFERENTIATION INTO ADIPOCYTES

TECHNICAL FIELD

The present invention relates to a culture medium and a method for inducing the in vitro differentiation of mammalian somatic stem cells into adipocytes.

BACKGROUND ART

Differentiation induction into adipocytes is used for confirmation of the undifferentiation ability of human somatic stem cells, research on metabolic syndromes and the like in differentiation-induced adipocytes, and other purposes.

Differentiation induction into adipocytes from human somatic stem cells and preadipocytes employs animal serum (such as fetal bovine serum or human serum). It is known that the component structure of animal serum has yet to be completely clarified, as well as capabilities such as the ability to induce differentiation into adipocytes vary depending on the origin of serum, the lot of product and the like. Thus, there is a problem that it is difficult to maintain the quality of adipocytes induced to differentiate under conditions of high serum concentration.

Conventionally, as methods for inducing the differentiation of somatic stem cells into adipocytes, there have been disclosed some methods such as a method using isobutylmethylxanthine, dexamethasone, insulin, and a thiazole derivative (such as rosiglitazone or pioglitazone) in an animal serum-containing culture medium (Non-patent Literature 1) and a method using isobutylmethylxanthine, dexamethasone, insulin, and an indole derivative (such as indomethacin) (Non-patent Literature 2). It is also known that the addition of biotin, prostaglandin, and pantothenic acid causes adipocyte differentiation.

Activation of RhoA is known to inhibit the induction of differentiation into adipocytes and promote the induction of differentiation into osteocytes (Non-patent Literature 3). Lysophosphatidic acid (LPA), which is lysophospholipid, is known as a substance that induces the RhoA activation. So far, there have been known no methods for improving the efficiency of differentiation into adipocytes by the addition of LPA serving to activate RhoA to a culture medium for inducing the differentiation of somatic stem cells into adipocytes.

PRIOR ART REFERENCES

Non-Patent Literature

[Non-patent Literature 1]: J Biol. Chem. 1995:28183-7.
[Non-patent Literature 2]: Stem Cells. 2005:1357-66.
[Non-patent Literature 3]: Dev Cell. 2004:483-95.

SUMMARY OF THE INVENTION

Problem to be Solved by the Invention

Conventionally, induction of the differentiation of mammalian somatic stem cells into adipocytes uses a differentiation inducing culture medium containing serum. The present invention is intended to provide a culture medium, an additive, and a method for efficiently inducing the differentiation of mammalian somatic stem cells into cells having the characteristics of adipocytes under conditions of serum-free or low-serum culture medium.

Means for Solving the Problem

The present inventors have conducted extensive research to find that mammalian somatic stem cells can be effectively differentiated into adipocytes under conditions of serum-free culture medium by adding to the culture medium an inducing agent conventionally used for differentiation induction of adipocytes, (such as isomethylxanthine, insulin, dexamethasone, rosiglitazone, or indomethacin), lysophosphatidic acid (LPA) as a ligand for endothelial cell differentiation gene (Edg) family receptors, biotin that is a vitamin known as a coenzyme of carboxylase, vitamin C(ascorbic acid or ascorbic acid 2-phosphate) as a vitamin having antioxidant functions, and HEPES that is an organic compound used as a buffer agent, and thereby have completed the present invention.

Specifically, the present invention provides a culture medium for inducing the differentiation of mammalian somatic stem cells into adipocytes, which culture medium includes a basal medium for culturing mammalian cells, an agent for inducing the differentiation of mammalian somatic stem cells into adipocytes, biotin, a ligand for endothelial cell differentiation gene (Edg) family receptors, vitamin C, and HEPES, and which culture medium is serum-free or contains a low concentration of serum. Furthermore, the present invention provides an additive to a culture medium for inducing the differentiation of mammalian somatic stem cells into adipocytes, which additive includes biotin, a ligand for endothelial cell differentiation gene (Edg) family receptors, vitamin C, and HEPES. Still furthermore, the present invention provides a method for inducing the differentiation of somatic stem cells into adipocytes, which method includes culturing the somatic stem cells that can differentiate into adipocytes in the culture medium according to the present invention described above.

Advantages of the Invention

The culture medium and the additive thereto according to the present invention enable somatic stem cells to be effectively differentiated into adipocytes under the conditions of not using serum added to conventional differentiation inducing culture media when inducing the differentiation of somatic stem cells into adipocytes, that is, under serum-free conditions. In addition, the present invention can eliminate influences of the origin and lot of serum on differentiation efficiency and the like caused by use of serum. As a result, differentiation-induced adipocytes with stable quality can be obtained.

BRIEF DESCRIPTION OF THE DRAWINGS

FIG. 1 shows diagrams obtained in Example 1 and Comparative Examples 1 to 3 in which cells induced to differentiate into adipocytes from human bone marrow-derived mesenchymal stem cells in respective culture media have been stained with oil red O.

FIG. 2 shows (A) a graph indicating changes in the quantity of adiponectin secreted from the cells induced to differentiate into adipocytes from human bone marrow-derived mesenchymal stem cells and (B) a graph indicating changes in the quantity of lipid stained with oil red O(in which the vertical axis represents values obtained by dividing absorbance at a wavelength of 492 nm by the number of cells), which were obtained in Example 1 and Comparative Examples 1 to 3.

FIG. 3 shows graphs indicating changes in the expression quantities (mRNA quantities) of (A) PPAR-gamma gene and (B) adiponectin gene in the cells induced to differentiate into adipocytes from human bone marrow-derived mesenchymal stem cells, which were obtained in Example 1 and Comparative Examples 1 to 3.

MODES FOR CARRYING OUT THE INVENTION

Figure 4:
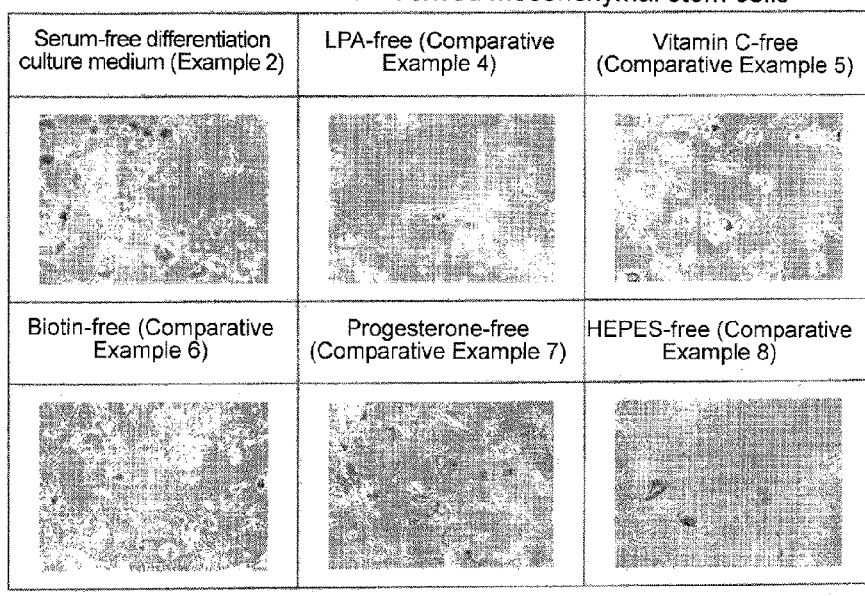
FIG. 4 shows diagrams obtained in Example 2 and Comparative Examples 4 to 8 in which cells induced to differentiate into adipocytes from human bone marrow-derived mesenchymal stem cells in respective culture media have been stained with oil red O.

In the present invention, "somatic stem cells" mean cells capable of transdifferentiate into one or more kinds of tissue cells forming each organ in vivo, such as osteoblasts, adipocytes, chondrocytes, skin cells, nerve cells, muscle cells, blood cells, fibroblasts, and hepatocytes. Additionally, the "somatic stem cells" are cells except embryonic stem cells in stem cells and precursor cells with the ability to differentiate into cells having some different kinds of functions, such as induced multipotent stem cells, hematopoietic stem cells, mesenchymal stem cells, neural stem cells, skin stem cells, hepatic stem cells, and pancreatic stem cells.

There is no restriction on cells that can be induced to differentiate into adipocytes in the culture medium of the present invention, as long as the cells are mammalian somatic stem cells (which include the precursor cells of adipocytes, as mentioned above). Preferable examples of the cells include somatic stem cells such as adipose tissue-derived stem cells, bone marrow-derived mesenchymal stem cells, and mesenchymal stem cells derived from fibrocytes and the like, although not restricted thereto.

The culture medium according to the present invention includes, as an essential component, a ligand for endothelial cell differentiation gene (Edg) family receptors exerting effects on RhoA activation. The Edg family receptors are a group of G protein-coupled receptors sharing a high degree of gene sequence homology, and receptors Edg-1 through Edg-8 have been identified to date in mammals such as humans, mice, and sheep. Among them, Edg-2, Edg-4, and Edg-7 are known to serve as LPA receptors and Edg-1, Edg-3, Edg-5, Edg-6, and Edg-8 are known to serve as S1P receptors. Additionally, "a ligand for receptors" means a substance coupled specifically to the receptors and includes not only natural ligands existing in vivo but also other natural or synthesized compounds known as agonists and antagonists.

The ligand for Edg family receptors (hereinafter referred to as "Edg ligand") is preferably one or more kinds of compounds selected from the group consisting of agonists such as lysophosphatidic acid (LPA) and a salt thereof.

The agonists for Edg family receptors are substances that couple to Edg family receptors to act like LPA. Examples of the agonists include sphingosine 1-phosphate (S1P), dihydrosphingosine 1-phosphate, platelet-activating factor (PAF), sphingosylphosphorylcholine, alkyl LPA analogues, and FTY 720.

LPA is a compound represented by the following general formula (I):

$$R\text{—}O\text{—}CH_2CH(OH)CH_2PO_4H_2 \quad (I)$$

(wherein R represents a $C_{10}$-$C_{30}$ alkyl group, a $C_{10}$-$C_{30}$ alkenyl group, or a $C_{10}$-$C_{30}$ acyl group). The carbon number of the acyl group as the R group in the above formula (I) does not include the carbon number of carbonyl group.

The salt of LPA may be a conventionally known salt, and examples of the salt of LPA include alkali metal salts such as sodium salt and potassium salt, and ammonium salts. As LPA or the salt thereof, there may be mentioned 1-oleoyl lysophosphatidic acid sodium salt, LPA potassium salt, and the like.

The Edg ligands may be used alone or in combination of two or more kinds thereof.

The culture medium of the present invention includes biotin that is a vitamin known for acting as a coenzyme for carboxylase. Biotin is known to play an important role in vivo as a coenzyme for pyruvate carboxylase involved in glucose metabolism, acetyl-CoA carboxylase and propionyl-CoA carboxylase involved in fatty acid metabolism, and the like.

The culture medium of the present invention includes vitamin C known as a water-soluble vitamin. Vitamin C is used for biosynthesis of amino acids and is also known for its important role in hydroxylation reactions proceeding in vivo, such as the secretion of hormone from the adrenal gland, the synthesis of L-carnitine as a carrier that transports fatty acids to mitochondria, and the production of collagen in connective tissue. Vitamin C may be ascorbic acid, ascorbic acid 2-phosphate, or a mixture thereof.

The culture medium of the present invention includes 2-[4-(2-hydroxyethyl)-1-piperazinyl]ethanesulfonic acid (HEPES) that is an organic compound used to prepare buffer solution. It is known that HEPES has a pKa of 7.55 (at 20 degrees C.) and has a buffering effect in the pH range of about 6.8 to 8.2.

The concentration of lysophosphatidic acid (LPA) and the salt thereof, which are the Edg ligand in the culture medium, preferably ranges from 0.01 to 100 μM, and more preferably ranges from 0.1 to 10 μM. The concentration of biotin and a salt thereof preferably ranges from 0.01 to 10 mM, and more preferably ranges from 0.1 to 5 mM. The concentration of vitamin C and a salt thereof preferably ranges from 0.01 to 10 mM, and more preferably ranges from 0.1 to 5 mM. The concentration of HEPES preferably ranges from 0.01 to 100 mM, and more preferably ranges from 0.1 to 50 mM.

The culture medium of the present invention includes an agent for inducing the differentiation of mammalian somatic stem cells into adipocytes. Agents for inducing the differentiation of somatic stem cells into adipocytes per se are known, and the present invention also can preferably use a known differentiation inducing agent. Preferable examples of the known differentiation inducing agent include isobutylmethylxanthine, insulin, dexamethasone, thiazole derivatives such as rosiglitazone and pioglitazone, and indole derivatives such as indomethacin. These differentiation inducing agents may be used alone or in combination of two or more kinds thereof.

The concentration of the differentiation inducing agent in the culture medium is appropriately determined in accordance with the kind of the differentiation inducing agent to be used, the kind of the cells to be used, and the like. The concentration of isobutylmethylxanthine ranges usually about from 10 to 1000 μM and preferably about from 250 to 750 μM. The concentration of insulin ranges usually about from 0.1 to 10 μM, and preferably about 0.5 to 2.5 μM. The concentration of dexamethasone ranges usually about from 0.1 to 10 μM, and preferably about from 0.5 to 2.5 μM.

The concentration of the thiazole derivative ranges usually about from 0.1 to 10 µM, and preferably about from 0.5 to 5 µM. The concentration of the indole derivative ranges usually about from 10 to 500 µM, and preferably about from 50 to 200 µM.

The culture medium of the present invention may be the same as a known mammalian cell culture medium except that the culture medium includes the above-described four kinds of essential components and the above-described differentiation inducing substance. Accordingly, the culture medium of the present invention can be obtained by adding to the known basal medium the above-described four kinds of essential components and the differentiation inducing agent conventionally used for inducing differentiation into adipocytes.

Preferable examples of a known serum-free basal medium that can be used for the culture medium of the present invention include minimum essential medium (MEM) such as Eagle's culture medium, Dulbecco's modified Eagle's medium (DMEM), minimum essential medium alpha (MEM-alpha), mesenchymal cell basal medium (MSCBM), Ham's F-12 medium and Ham's F-10 medium, DMEM/F12 medium, William's medium E, RPMI-1640 medium, MCDB medium, medium 199, Fisher's medium, Iscove's modified Dulbecco's medium (IMDM), and McCoy's modified medium. These culture media are all those known in this field.

The culture medium of the present invention may further include various additives that are known to be included in mammalian cell culture media. As examples of such known additives, there may be mentioned amino acids, inorganic salts, vitamins, and other additives such as carbon sources and antibiotics.

As the amino acids, there may be mentioned glycine, L-alanine, L-arginine, L-asparagine, L-aspartic acid, L-cysteine, L-cystine, L-glutamic acid, L-glutamine, L-histidine, L-isoleucine, L-leucine, L-lysine, L-methionine, L-phenylalanine, L-proline, L-serine, L-threonine, L-tryptophan, L-tyrosine, and L-valine.

As the inorganic salts, there may be mentioned calcium chloride, copper sulfate, iron (III) nitrate, iron sulfate, magnesium chloride, magnesium sulfate, potassium chloride, sodium hydrogen carbonate, sodium chloride, disodium hydrogenphosphate, sodium dihydrogenphosphate, and zinc sulfate.

As the vitamins, there may be mentioned choline, vitamin A, vitamin B1, vitamin B2, vitamin B3, vitamin B4, vitamin B5, vitamin B6, Vitamin B7, vitamin B12, vitamin B13, vitamin B15, vitamin B17, vitamin Bh, vitamin Bt, vitamin Bx, vitamin D, vitamin E, vitamin F, vitamin K, vitamin M, and vitamin P.

The addition of these additives to a mammalian cell culture medium per se is known. The quantity of each additive to be added may also be the same as that in a known culture medium and can be appropriately determined by routine testing. For example, the quantity of the amino acids to be added ranges usually about from 5 mg/L to 500 mg/L for each amino acid, and preferably about from 10 mg/L to 400 mg/L; the quantity of the inorganic salts to be added ranges usually from about 0 mg/L to 10 g/L, and preferably from about 0.01 mg/L to 7 g/L; and the quantity of the vitamins to be added ranges from about 0.01 mg/L to 500 mg/L for each vitamin, and preferably from about 0.05 mg/L to 300 mg/L.

As other additives, there may be mentioned (1) growth factors such as fibroblast growth factor (FGF), endothelial growth factor (EGF), and platelet-derived growth factor (PDGF), (2) antibiotics such as penicillin, streptomycin, gentamicin, and kanamycin, (3) carbon sources such as glucose, galactose, fructose, and sucrose, (4) trace metals such as magnesium, iron, zinc, calcium, potassium, sodium, copper, selenium, cobalt, tin, molybdenum, nickel, and silicon, (5) antioxidants such as 2-mercaptoethanol, catalase, superoxide dismutase, and N-acetylcysteine, and other additives such as adenosine 5'-monophosphate, corticosterone, ethanolamine, insulin, reduced glutathione, lipoic acid, hypoxanthine, phenol red, progesterone, putrescine, pyruvic acid, thymidine, triiodothyronine, transferrin, and lactoferrin. The quantities of these additives to be added may also be the same as those in the conventional art, and can also be appropriately determined by routine testing in accordance with the purpose of each additive. The quantity of each additive ranges usually about from 0.001 mg/L to 5 g/L, and particularly about from 0.1 to 3 g/L.

The culture medium of the present invention can include one or more kinds of the various additives described above and usually includes a combination of plural kinds of additives.

Among the other additives, progesterone is preferable since it exhibits an effect of increasing the quantity of lipid droplets in adipocytes when added to the culture medium. The preferable concentration of progesterone in the culture medium ranges about from 20 nM to 200 nM.

The culture medium of the present invention is serum-free or contains a low concentration of serum, and preferably it is serum-free. In this case, the culture medium with "a low concentration of serum" means the culture medium that contains serum whose content is 5% by weight or lower, and preferably 1% by weight.

In the culture medium of the present invention, culturing of mammalian somatic cells per se can be conducted in the same manner as the conventional art and is usually conducted at a temperature of 30 to 37 degrees C. under the environments of 5% $CO_2$ and 5 to 21% $O_2$. In addition, culturing time required for differentiation induction can be appropriately determined by the kinds of the differentiation inducing agent, the cells, and the like to be used, and also can be appropriately determined by observing the conditions of the cells. Usually, the culturing time ranges about from 10 days to 28 days.

The present invention also provides an additive for forming the above-described culture medium of the present invention. Thus, the additive according to the present invention includes the above-described Edg ligand, biotin, vitamin C, and HEPES. In addition to them, the additive of the present invention may further include the above-described differentiation inducing agent. Furthermore, the additive may include one or more kinds of the additives described above. Still furthermore, the additive may contain the component of the basal medium so as to provide the culture medium of the present invention by being merely dissolved in water. Conveniently and preferably, the additive of the present invention has a composition that provides the above-described culture medium of the present invention by being dissolved in water or the basal medium. In this case, the mixing ratio of each component contained in the additive is the same as the ratio of the content of each component in the culture medium. As the basal medium, there may be mentioned the above-described various culture media that are conventionally used for culturing mammalian cells.

Hereinafter, the present invention will be explained in more detail based on Examples and Comparative Examples, although the invention is not restricted to the Examples below. Concentrations mentioned in each Example are the final concentrations in the culture medium. The lysophosphatidic acid (LPA) used was all 1-oleoyl lysophosphatidic acid sodium.

EXAMPLES

Example 1 and Comparative Examples 1 to 3

Differentiation Induction of Human Bone Marrow-Derived Mesenchymal Stem Cells into Adipocytes Under Serum-Free Conditions 1

A serum-free control culture medium (Comparative Example 1) was produced by adding 5 μM of LPA, 1 mM of vitamin C, 100 μM of biotin, and 41.5 nM of progesterone to Dulbecco's modified Eagle's medium (DMEM) containing HEPES (concentration of 25 mM).

To HEPES-containing DMEM, at the final concentrations, 500 μM of isobutylmethylxanthine (IBMX), 1 μM of dexamethasone, 1 μM of insulin, and 1 μM of rosiglitazone were added to produce an adipocyte differentiation inducing culture medium.

To the above adipocyte differentiation inducing culture medium, 5 μM of LPA, 1 mM of vitamin C, 100 μM of biotin, and 41.5 nM of progesterone were added to produce a serum-free differentiation inducing culture medium according to the present invention (hereinafter referred to as serum-free differentiation culture medium: Example 1).

To each of HEPES-containing DMEM and the adipocyte differentiation inducing culture medium, 10% of fetal bovine serum (FBS) was added to produce a conventional culture medium (Comparative Example 2) and a conventional differentiation culture medium (Comparative Example 3).

Human bone marrow-derived mesenchymal stem cells (strain name: normal human mesenchymal stem cells (Cryo hMSC purchased from LONZA) were seeded in a culture container with a 48-hole culture plate at a cell density of 30,000 cells/cm². These culture media were replaced with respective fresh ones every three to four days to culture the cells at 37 degrees C. and 5% $CO_2$ for 7 to 21 days, thereby inducing differentiation into adipocytes.

The adipocytes were confirmed by oil red 0 staining of lipid droplets accumulated in the cells. Additionally, the oil red O-stained cells were extracted with isopropanol to measure the quantity of lipid accumulated in the cells using an absorption spectrophotometer (wavelength of 492 nm). Then, the quantities of adiponectin secreted from the cells in the three days: Day 4 to Day 7, Day 11 to Day 14, and Day 18 to Day 21 of differentiation induction were confirmed using an adiponectin ELISA kit (Fujirebio Inc). Furthermore, the mRNA expressions of PPAR-gamma and adiponectin were confirmed by real-time PCR. The forward and reverse primers for PPRA-gamma used were ggtttcagaaatgccttgcag (SEQ ID NO:1) and tcgcctttgctttggtcag (SEQ ID NO:2), respectively; the forward and reverse primers for adiponectin used were ccctcccgatatcaaaaagact (SEQ ID NO:3) and tcagaaacaggca-cacaactca (SEQ ID NO:4), respectively; and the forward and reverse primers for GAPDH used were aacagcctcaagatcat-cagc (SEQ ID NO:5) and ggatgatgttctggagagcc (SEQ ID NO:6), respectively.

FIGS. 1 to 3 show the results. In FIGS. 1 to 3, it was confirmed that the human bone marrow-derived mesenchymal stem cells were efficiently induced to differentiate into adipocytes in the serum-free culture medium of the present invention, as in the conventional serum-containing differentiation inducing culture medium.

Example 2 and Comparative Examples 4 to 7

Differentiation Induction of Human Bone Marrow-derived Mesenchymal Stem Cells into Adipocytes Under Serum-free Conditions 2

As in Example 1, at the final concentrations, 500 μM of IBMX, 1 μM of dexamethasone, 1 μM of insulin, and 1 μM of rosiglitazone were added to HEPES-containing DMEM to produce an adipocyte differentiation inducing culture medium. To the adipocyte differentiation inducing basal medium, 5 μM of LPA, 1 mM of vitamin C, 0.5 mM of biotin, and 41.5 nM of progesterone were added to produce a serum-free differentiation culture medium according to the present invention (Example 2). On the other hand, for comparison, there were also prepared a culture medium without LPA alone (Comparative Example 4), a culture medium without vitamin C alone (Comparative Example 5), a culture medium without biotin alone (Comparative Example 6), and a culture medium without progesterone alone (Comparative Example 7).

To DMEM not containing HEPES, at the final concentrations, 500 μM of IBMX, 1 μM of dexamethasone, 1 μM of insulin, and 1 μM of rosiglitazone were added to produce an adipocyte differentiation inducing culture medium 2. To the adipocyte differentiation inducing basal medium 2, 5 μM of LPA, 1 mM of vitamin C, 100 μM of biotin, and 41.5 nM of progesterone were added to produce a serum-free differentiation culture medium 2 (Comparative Example 8).

As in Example 1, human bone marrow-derived mesenchymal stem cells were seeded in the wells of a 48-hole culture plate at the cell density of 30,000 cells/cm². These culture media were replaced with fresh ones every three to four days to culture the cells at 37 degrees C. and 5% $CO_2$ for 21 days, thereby inducing differentiation into adipocytes.

The adipocytes were confirmed by staining lipid droplets accumulated in the cells with oil red 0, as in Example 1.

FIG. 4 shows the results. As shown in FIG. 4, the quantity of lipid droplets in the adipocytes was obviously smaller in the culturing of the cells in the culture media of Comparative Examples 4 to 6 and 8 as compared to the culturing in the culture media of Example 2 and Comparative Example 7. This indicated that LPA, vitamin C, biotin, and HEPES are substances necessary to induce the differentiation of the human bone marrow-derived mesenchymal stem cells into adipocytes, whereas progesterone is not essential for the differentiation induction.

Example 3 and Comparative Examples 9 to 11

Differentiation Induction of Human Multipotent Adipose-derived Stem Cells into Adipocytes Under Serum-free Conditions As in Example 1, 5 μM of LPA, 1 mM of vitamin C, 100 μM of biotin, and 41.5 nM of progesterone were added to HEPES-containing DMEM to produce a serum-free control culture medium (Comparative Example 9).

As in Example 1, at the final concentrations, 500 μM of IBMX, 1 μM of dexamethasone, 1 μM of insulin, and 1 μM of rosiglitazone were added to HEPES-containing DMEM to produce an adipocyte differentiation inducing culture medium. To the adipocyte differentiation inducing basal medium, 5 μM of LPA, 1 mM of vitamin C, 100 μM of biotin, and 41.5 nM of progesterone were added to produce a serum-free differentiation culture medium (Example 3).

To each of HEPES-containing DMEM and the adipocyte differentiation inducing culture medium, 10% of fetal bovine serum (FBS) was added to produce a conventional culture medium (Comparative Example 10) and a conventional differentiation culture medium (Comparative Example 11).

Human multipotent adipose-derived stem cells (strain name: hMADS cells purchased from Stem Cell Science Inc.) were seeded in the wells of a 48-hole culture plate at the cell density of 30,000 cells/cm². These culture media were replaced with respective fresh ones every three to four days to culture the cells at 37 degrees C. and 5% $CO_2$ for 14 days, thereby inducing differentiation into adipocytes.

As in Example 1, the adipocytes were confirmed by oil red 0 staining of lipid droplets accumulated in the cells.

Figure 5:
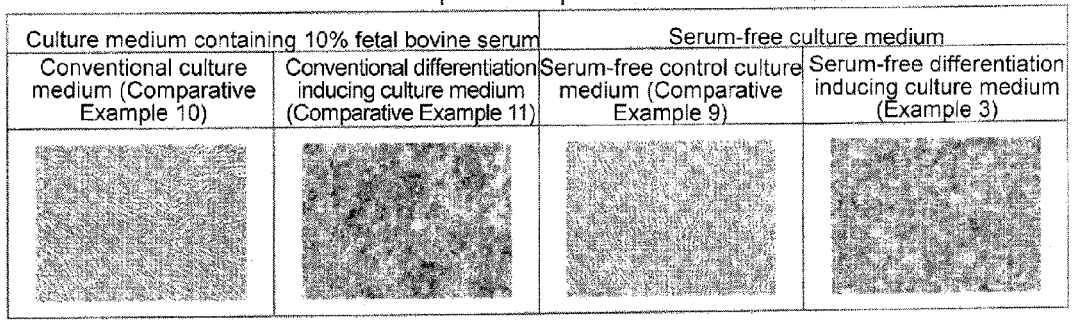
FIG. 5 shows diagrams obtained in Example 3 and Comparative Examples 9 to 11 in which cells induced to differentiate into adipocytes from human multipotent adipose-derived stem cells in respective culture media have been stained with oil red O.

FIG. 5 shows the results. As shown in FIG. 5, adipocytes were not induced in Comparative Example 8 (serum-free control culture medium) and Comparative Example 9 (conventional culture medium). On the other hand, in the culturing in the culture medium of Example 3, many adipocytes were efficiently differentiated in the same extent as the culturing in the culture medium of Comparative Example 10 (conventional differentiation culture medium containing serum).

Example 4 and Comparative Examples 12 to 14

Differentiation Induction of Human Preadipocytes into Adipocytes Under Serum-free Conditions The same operations as in Example 3 and Comparative Examples 9 to 11 were performed except that the human multipotent adipose-derived stem cells were replaced by human preadipocytes (strain name: normal human preadipocyte cells visceral preadipocytes (Cryo HPRAD-VICE) purchased from LONZA) (Example 4 and Comparative Examples 12 to 14, respectively).

Figure 6:
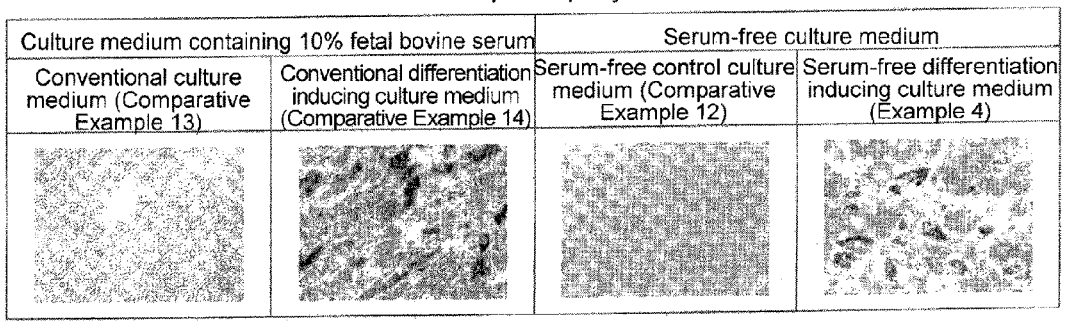
FIG. 6 shows diagrams obtained in Example 4 and Comparative Examples 12 to 14 in which cells induced to differentiate into adipocytes from human preadipocytes in respective culture media have been stained with oil red O.

FIG. 6 shows the results. As shown in FIG. 6, adipocytes were not induced in Comparative Example 12 (serum-free control culture medium) and Comparative Example 13 (conventional culture medium). On the other hand, in the culturing in the culture medium of Example 4, many adipocytes were efficiently differentiated in the same extent as that in the culture medium of Comparative Example 14 (conventional differentiation culture medium containing serum).

Sequence Listing

The invention claimed is:

1. A culture medium for inducing differentiation of mammalian somatic stem cells into adipocytes, comprising a basal medium for culturing mammalian cells, an agent for inducing the differentiation of mammalian somatic stem cells into adipocytes, biotin, a ligand for endothelial cell differentiation gene (Edg) family receptors, vitamin C, and HEPES, which culture medium is serum-free.

2. The culture medium according to claim 1, wherein, in the culture medium, the concentration of the ligand for Edg family receptors ranges from 0.01 μM to 100 μM the concentration of biotin ranges from 10 μM to 10 mM, the concentration of vitamin C ranges from 10 μM to 10 mM, and the concentration of HEPES ranges from 10 μM to 100 mM.

3. The culture medium according to claim 1 or 2, wherein the ligand for Edg family receptors is at least one selected from the group consisting of lysophosphatidic acid (LPA) and salts thereof, sphingosine 1-phosphate (S1P), and agonists for Edg family receptors.

4. The culture medium according to claim 1, wherein the differentiation inducing agent is at least one selected from the group consisting of isobutylmethylxanthine, insulin, dexamethasone, rosiglitazone, pioglitazone, and indomethacin.

5. The culture medium according to claim 1, wherein the basal medium is selected from the group consisting of DMEM, MEM alpha, MEM, Ham's F-12, RPMI-1640, DMEM/F12, William's medium E, MCDB medium, Medium 199, Fisher's medium, Iscove's modified Dulbecco's medium (IMDM), and McCoy's modified medium.

6. An additive to a culture medium for inducing the differentiation of mammalian somatic stem cells into adipocytes, the additive comprising biotin, a ligand for endothelial cell differentiation gene (Edg) family receptors, vitamin C, and HEPES.

7. The additive according to claim 6, further comprising an agent for inducing the differentiation of somatic stem cells into adipocytes.

8. The additive according to claim 6 or 7 having a composition that provides a culture medium by being dissolved in a basal medium, said culture medium being a culture medium for inducing differentiation of mammalian somatic stem cells into adipocytes, said culture medium comprising said basal medium for culturing mammalian cells, an agent for inducing the differentiation of mammalian somatic stem cells into adipocytes, biotin, a ligand for endothelial cell differentiation gene (Edg) family receptors, vitamin C, and HEPES, which culture medium is serum-free.

9. A method for inducing differentiation of somatic stem cells into adipocytes, the method comprising culturing the somatic stem cells that can differentiate into adipocytes in the culture medium according to claim 1, wherein the somatic stem cells are selected from the group consisting of human bone marrow-derived mesenchymal stem cells and human multipotent adipose-derived stem cells.

10. The culture medium according to claim 1, wherein the ligand for Edg family receptors is lysophosphatidic acid (LPA) and salts thereof.

11. The culture medium according to claim 1, wherein the differentiation inducing agent is isobutylmethylxanthine.

12. The culture medium according to claim 1, wherein the basal medium is DMEM.

\* \* \* \* \*

```
SEQUENCE LISTING

<160> NUMBER OF SEQ ID NOS: 6

<210> SEQ ID NO 1
<211> LENGTH: 21
<212> TYPE: DNA
<213> ORGANISM: artificial
<220> FEATURE:
<223> OTHER INFORMATION: forward primer for amplifying PPAR-gamma cDNA

<400> SEQUENCE: 1
ggtttcagaa atgccttgca g                                                  21

<210> SEQ ID NO 2
<211> LENGTH: 19
<212> TYPE: DNA
<213> ORGANISM: artificial
<220> FEATURE:
<223> OTHER INFORMATION: reverse primer for amplifying PPRA-gamma cDNA

<400> SEQUENCE: 2
tcgcctttgc tttggtcag                                                     19

<210> SEQ ID NO 3
<211> LENGTH: 22
<212> TYPE: DNA
<213> ORGANISM: artificial
<220> FEATURE:
<223> OTHER INFORMATION: forward primer for amplifying adiponectin cDNA

<400> SEQUENCE: 3
ccctcccgat atcaaaaaga ct                                                 22

<210> SEQ ID NO 4
<211> LENGTH: 22
<212> TYPE: DNA
<213> ORGANISM: artificial
<220> FEATURE:
<223> OTHER INFORMATION: reverse primer for amplifying adiponectin cDNA

<400> SEQUENCE: 4
tcagaaacag gcacacaact ca                                                 22

<210> SEQ ID NO 5
<211> LENGTH: 21
<212> TYPE: DNA
<213> ORGANISM: artificial
<220> FEATURE:
<223> OTHER INFORMATION: forward primer for amplifying GAPDH cDNA

<400> SEQUENCE: 5
```

```
aacagcctca agatcatcag c                                          21

<210> SEQ ID NO 6
<211> LENGTH: 20
<212> TYPE: DNA
<213> ORGANISM: artificial
<220> FEATURE:
<223> OTHER INFORMATION: reverse primer for amplifying GAPDH cDNA

<400> SEQUENCE: 6
ggatgatgtt ctggagagcc                                            20
```